United States Patent [19]
Ross

[11] Patent Number: 5,549,639
[45] Date of Patent: Aug. 27, 1996

[54] NON-INVASIVE HYPERTHERMIA APPARATUS INCLUDING COAXIAL APPLICATOR HAVING A NON-INVASIVE RADIOMETRIC RECEIVING ANTENNA INCORPORATED THEREIN AND METHOD OF USE THEREOF

[75] Inventor: Michael P. Ross, Albquuerque, N.M.

[73] Assignee: Sandia Corporation, Albuquerque, N.M.

[21] Appl. No.: 307,957

[22] Filed: Sep. 16, 1994

[51] Int. Cl.⁶ .................................................. A61N 5/02
[52] U.S. Cl. ........................ 607/101; 607/102; 607/154
[58] Field of Search ..................................... 219/690, 695, 219/696, 710, 748; 353/222, 243, 245; 607/101, 102, 154–156

[56] References Cited

U.S. PATENT DOCUMENTS

| | | | |
|---|---|---|---|
| 4,051,449 | 9/1977 | Fincke et al. | 333/222 |
| 4,197,860 | 4/1980 | Sterzer | 128/804 |
| 4,311,154 | 1/1982 | Sterzer et al. | 607/102 |
| 4,342,972 | 8/1982 | Nishikawa et al. | 333/222 |
| 4,506,241 | 3/1985 | Makimoto . | |
| 4,633,875 | 1/1987 | Turner | 128/422 |
| 4,662,383 | 5/1987 | Sogawa et al. | 607/156 |
| 4,934,365 | 6/1990 | Morgenthaler | 128/399 |
| 5,323,778 | 6/1994 | Kandorpa et al. | 607/101 |
| 5,369,251 | 11/1994 | King et al. | 607/156 |
| 5,370,676 | 12/1994 | Sozanski et al. | 607/102 |

OTHER PUBLICATIONS

Gautherie (Ed), "Methods of Hyperthermia Control," Springer–Verlag, pp. 47–58 and pp. 119–128.
Ross, M. P. and Williams, J. T., "A Novel Dual–Function Microwave Hyperthermic/Radiometric Antenna," Proceedings–Microwave and Medicine Conference, Rome, Italy, 4 pp. Oct., 1993.

Primary Examiner—Angela D. Sykes
Assistant Examiner—Robert L. Nasser, Jr.
Attorney, Agent, or Firm—Gregory A. Cone; Thomas C. Auchterlonie

[57] ABSTRACT

A coaxial hyperthermia applicator for applying non-invasively electromagnetic energy to a body against which it is placed. The coaxial applicator antenna has formed integrally within it a non-invasive radiometric antenna for receiving thermoelectromagnetic emissions. The coaxial-configured applicator produces a bell-shaped radiation pattern symmetric about the axis of symmetry of the coaxial applicator. Integrating the radiometric antenna within the coaxial applicator produces a single device that performs dual functions. The first function is to transmit non-invasively energy for heating a subcutaneous tumor. The second function is to receive non-invasively thermal electromagnetic radiation from the tumor by which temperature is sensed and fed back to control the output of the coaxial applicator.

15 Claims, 10 Drawing Sheets

BOLUS: h = 1 cm
$E_{r1} = 81$
$\sigma_1 = 0 \, S/m$

BODY: $E_{r2} = 50$
$\sigma_2 = 1.5 \, S/m$
$f = 500 \, MHz$
$a = 1.5 \, cm$
$b = 3.0 \, cm$ BOLUS: h = 1 cm
$E_{r1} = 81$
$\sigma_1 = 0\,S/m$ BODY: $E_{r1} = 50$
$\sigma_2 = 1.5\,S/m$
f = 900 MHz
a = 1.5 cm
b = 3.0 cm

NON-INVASIVE HYPERTHERMIA APPARATUS INCLUDING COAXIAL APPLICATOR HAVING A NON-INVASIVE RADIOMETRIC RECEIVING ANTENNA INCORPORATED THEREIN AND METHOD OF USE THEREOF

STATEMENT AS TO RIGHTS TO INVENTIONS MADE UNDER FEDERALLY-SPONSORED RESEARCH AND DEVELOPMENT

The government has rights to this invention pursuant to contract number DE-AC04-76PD00789, awarded by the U.S. Department of Energy.

FIELD OF INVENTION

The invention is for use in the medical field of hyperthermia treatment, i.e., heating tissue via electromagnetic radiation.

BACKGROUND OF THE INVENTION

It is well known among medical practitioners that a patient with a cancerous tumor can be treated successfully by a process which raises the temperature of the tumor. This treatment is generally referred to as hyperthermia. Remission of a tumor can be affected by elevating its temperature to $40° \leq T \leq 44°$ C. It is desirable to provide for a uniform temperature distribution within the treated tissue.

One method of hyperthermia treatment is the use of electromagnetic radiation energy. The temperature of the tissue irradiated by the energy is a function of the power or intensity of the signal applied to the surface of the body tissue. The depth of penetration into the body is an inverse function of the signal frequency employed. The volume of the tissue to be treated is controlled by the electrical and geometrical design of the signal applicator. It is known that a flexible applicator can be utilized to conform to irregular surfaces.

Electromagnetic applicators radiate waves which propagate at the speed of light, 300,000 km/sec in a vacuum, or slower in matter. Such waves are characterized by both a propagation direction and a vector polarization.

Prior methods of hyperthermia treatment employ a waveguide applicator to supply the signal for irradiation of the treated tissue. The distribution of the irradiating signal from the waveguide applicator is manifested as a pattern of standing waves of the operating frequency. The standing wave distribution produces maximum and minimum voltage points which develop non-uniform irradiating signals, correspondingly producing undesirable non-uniform heating of the treated tissue.

An optimal non-invasive applicator delivers maximum power to the tumor while minimally heating surrounding healthy tissue. Since waves attenuate, i.e., deposit power, as they penetrate lossy tissue, a focusing source arrangement is required. Constructive interference at the tumor is obtained by adjusting the phase and amplitude of each point of the signal source. For constructive interference at the focal point, the electrical field at the tissue surface must be properly aligned and phased so that waves propagating along all paths in the entire tissue volume arrive in the same fashion. Merely adjusting phase, polarization, and amplitude for maximum focusing, however, does not necessarily produce an acceptable power-density distribution. It remains a problem that certain areas receive significantly more energy than adjacent areas, i.e., non-uniform heating.

It is well known that waveguide transmission lines can efficiently conduct or transmit electromagnetic energy. Waveguides such as this that are useful for carrying electromagnetic energy in the frequency range below one gigahertz, however, are also generally large and cumbersome unless they are dielectrically loaded, or filled, with a dielectric material having a dielectric constant substantially greater than unity.

A further requirement of applicators is a capacity to monitor power being deposited in the exposed tissue. Applied dosage information may be used as an approximate substitute for the difficult problem of direct, non-invasive temperature measurement.

Specific prior art hyperthermia techniques and apparatus therefor include: U.S. Pat. No. 4,197,860 issued 15 Apr. 1980 to Sterzer; U.S. Pat. No. 4,633,875 issued 6 Jan. 1987 to Turner; and U.S. Pat. No. 4,934,365 issued 19 Jun. 1990 to Morgenthaler.

U.S. Pat. No. 4,179,860 discloses a hyperthermia applicator and feedback control using a completely independent, i.e., non-integrated, albeit non-invasive, radiometer for sensing temperature of the heated tissue. When the sensed temperature exceeds the upper bound of a desired range, heating is inhibited. Heating is restarted after the sensed temperature falls below the lower bound of the desired range. The antenna in the applicator is a flat array of printed dipoles that does not act as a coaxially structured antenna and thus fails to produce a transverse electromagnetic (TEM) mode. Further, the antenna suffers the problem of producing dispersed hot spots. Also, nothing is disclosed or suggested about regulating the temperature of the dielectric within the applicator.

U.S. Pat. No. 4,633,875 discloses a hyperthermia applicator of waveguide construction having feedback control, albeit employing invasive temperature sensors. Invasive techniques are not desirable because they increase the trauma to the patient and risk the mixing of abnormal cells (those being treated) into healthy tissue. Here also, the rectangular waveguide does not operate in the TEM mode.

U.S. Pat. No. 4,934,365 discloses a hyperthermia applicator of troughguide construction which also suffers the problem of dispersed hot spots. It merely suggests the possibility of electronic feedback control, stopping short of suggesting thermometry feedback (be it invasive or noninvasive). Here, the radiometry employed is not microwave radiometry nor is the TEM mode produced.

Other attempts have been made to use the same antenna structure for both transmitting/heating and radiometry purposes. But since radiometry is best suited to using multifrequencies ranging from 1 to 4 GHz and the applicator is best suited to using one frequency between 100 MHz and 1 GHz, such a dual-function antenna has to be very broadband. No one has had success with such an arrangement.

Thus, the prior art has failed to teach an applicator having incorporated therein a radiometric receiving antenna. Further, the prior art has failed to teach such a combined antennas producing a TEM mode having a principal, non-dispersed maxima.

SUMMARY OF THE INVENTION

It is an object of the present invention to provide an integrated, dual-functional hyperthermia apparatus for both non-invasive heating and sensing temperature non-invasively (for feedback control).

It is an object of the present invention that the construction of the applicator be a modified horn.

It is an object of the present invention that the applicator be coupled to the body using a bolus interface, the bolus being filled with dielectric.

It is an object of the present invention that an interior space of the applicator and an interior space of the bolus be continuous, and that this continuous space be filled with dielectric.

It is an object of the present invention that the temperature of the dielectric, that fills the common space formed by the interiors of the applicator and the bolus, be regulated, thereby enhancing not only the comfort of the patient in the region of her body which contacts the bolus, but also maintaining a uniform radiometric thermometry receiving antenna temperature, which reduces thermal noise fluctuations.

The objects of the present invention are fulfilled by a coaxial-configured modified horn applicator having integrated therein a discrete radiometric receiving antenna. A discrete radiometric receiving antenna is integrated within a central interior space of the coaxial-configured applicator. This has the advantage of eliminating the need for two separate structures for heating and sensing, respectively. The coaxial-configured modified horn applicator, irrespective of the presence of radiometric receiving antenna, produces the TEM mode of energy propagation that causes the heating pattern to be a maximum in the area of the body centrally located along an axis of propagation of the applicator. The integrated nature of the receiving antenna takes advantage of this radiation pattern because the field of view of the receiving antenna is in substantially the same location as the area of the greatest amount of heating. This has the further advantage of focusing the principal maxima in the principal area sensed by the receiver antenna, thereby enhancing feedback accuracy.

The foregoing and other objectives of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention and wherein . . .

DETAILED DESCRIPTION OF THE PREFERRED EMBODIMENTS

Figure 1:
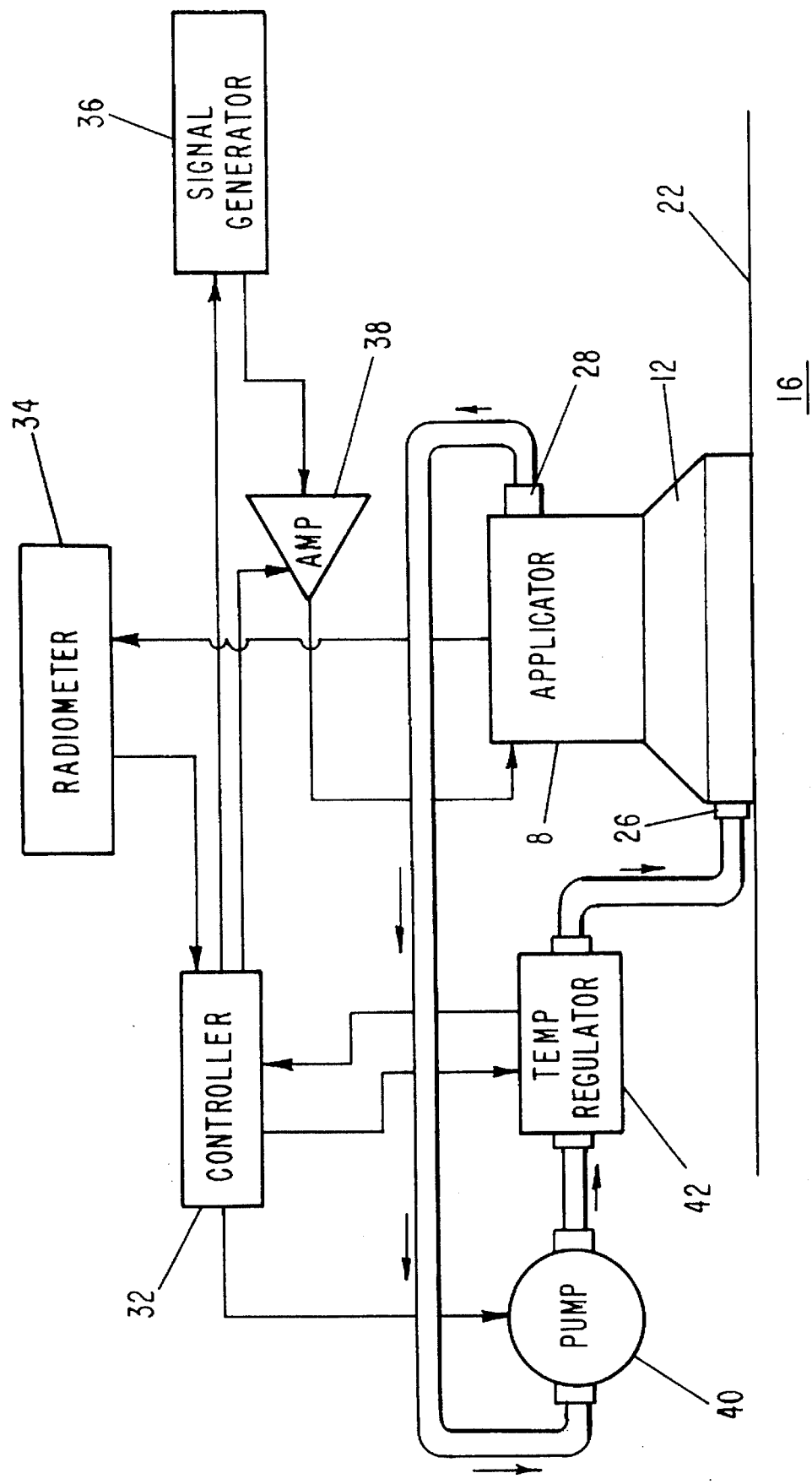
FIG. 1 depicts the overall structure of a preferred embodiment of the present application.

FIG. 1 depicts the overall structure of the preferred embodiments of the present application. A non-invasive, coaxial-configured, energy transmitting antenna, i.e., hyperthermia applicator, 8 having integrated therein a discrete non-invasive thermometry receiving, i.e., radiometric, antenna 10 FIG. 2 (that receives thermoelectromagnetic emissions related to temperature), is placed against a body 16 at a body interface 22. A controller 32 provides a signal to a signal generator 36, which responsively generates a transmission signal for the transmitting antenna, i.e., applicator, 8 (discussed later).

An amplifier 38 amplifies the transmission signal before it reaches the transmitting antenna 8. A single or multifrequency radiometer 34 receives a signal from the discrete radiometric receiving antenna 10 FIG. 2 integrated within the coaxial-configured applicator 8 (discussed below) and outputs a radiometric signal to the controller 32. Within the interior space of the applicator 8 is a liquid dielectric 12. The liquid dielectric 12 is circulated within that interior space, entering at a input 26 and exiting from a output 28. The dielectric 12 is circulated by a pump 40 and its temperature is regulated by a temperature regulator 42. The signal generator 36, amplifier 38 and multifrequency radiometer 34 are well known in the art and will not be discussed further. As to pump 40 and temperature regulator 42, they too are well-known, and are usually commercially available as a combined "constant temperature bath/circulator" unit, for example, as sold by the NESLAB company.

Figure 2:
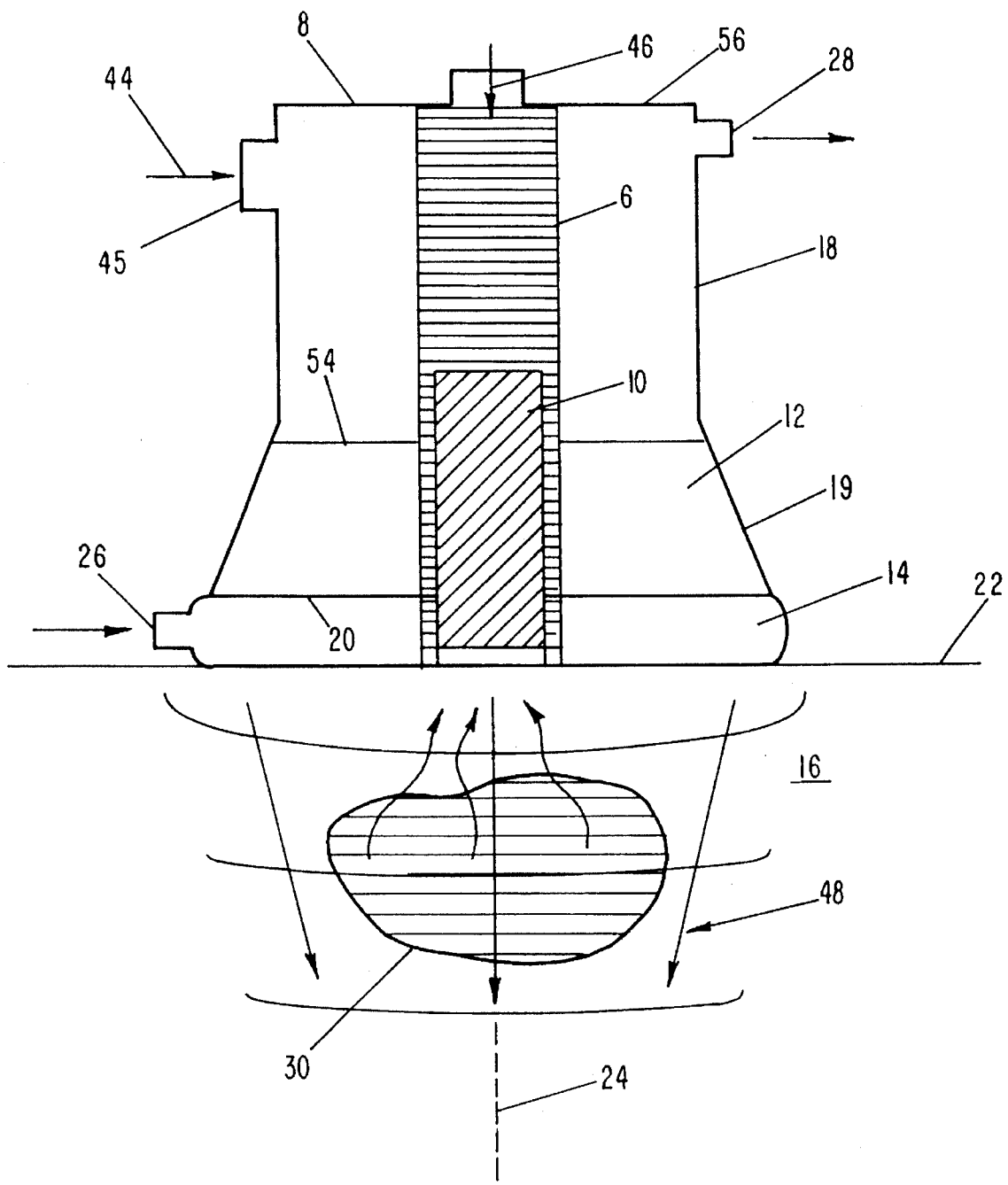
FIG. 2 depicts in greater detail the non-invasive hyperthermia applicator and non-invasive thermometry receiving antenna integrated therein shown generally in FIG. 1.

FIG. 2 depicts in greater detail the coaxial-configured antenna 8, having integrally constructed therein the non-invasive thermometry receiving antenna. The applicator 8 is constructed as a modified horn that acts as a coaxial resonator and is connected to a bolus interface 14 for coupling the applicator 8 to the body 16 at the body interface 22. An interior space of the applicator 8 and the bolus 14 are continuous and this space is filled with the dielectric 12. The dielectric 12 preferably has a permittivity substantially equal to that of the human body, e.g., deionized water.

The applicator 8 is a modified horn constructed as coaxial conductor-cylinders 6 (inner/center) and 18 (outer). A cylinder is defined by a surface generated by a straight line moving parallel to a fixed straight line and intersecting a plane curve, but here the inner and outer conductors are preferably substantially right circular cylinders, i.e., two cylinders whose cylindrical surfaces pass through concentric circles in a given plane and are perpendicular to this plane, connected by shorting-end conductor 56 perpendicular thereto, respectively. Outer conductor 18 has a flared portion 19, or skirt, in the shape of a cone (with its apex removed) connected to bolus 14. In the alternative, outer conductor 18 could be in the shape of a cone or triangle (each with its apex removed) or a rectangle or square; the same is true for inner conductor 6. In this alternative circumstance, the diameter of outer conductor 18 at the end connected to shorting-end conductor 56 would be smaller than the diameter at the end opposite thereof.

This modified horn acts like a coaxial resonator, i.e., a resonator including a length of coaxial line short-circuited at one end, that produces a very desirable radiation pattern (to be discussed below). The modified horn's three principal conducting surfaces (6, 18 and 56) are made of a conducting material, preferably metal.

Figure 3:
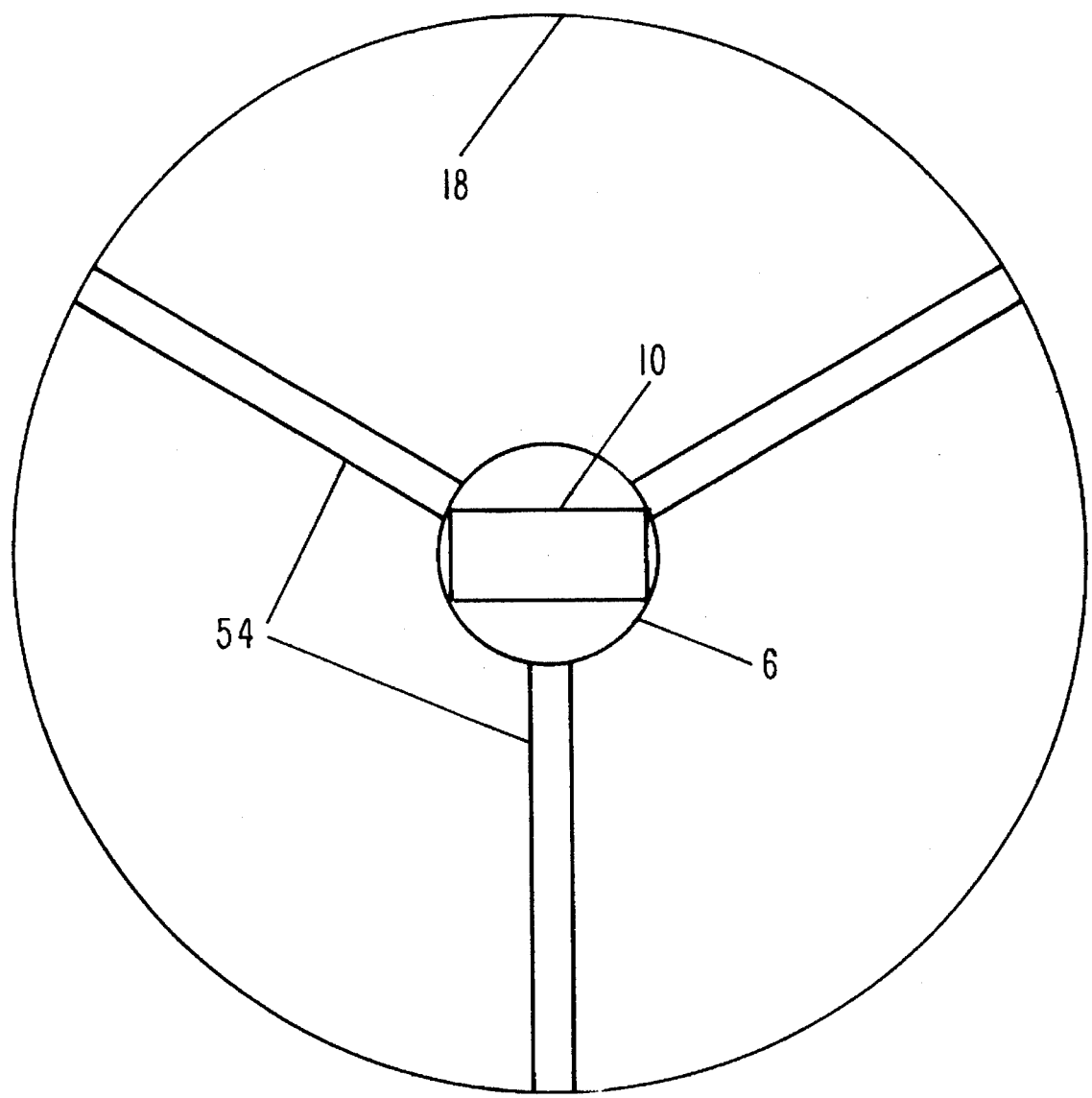
FIG. 3 depicts a cross-section of the applicator of FIG. 2.
Figure 4:
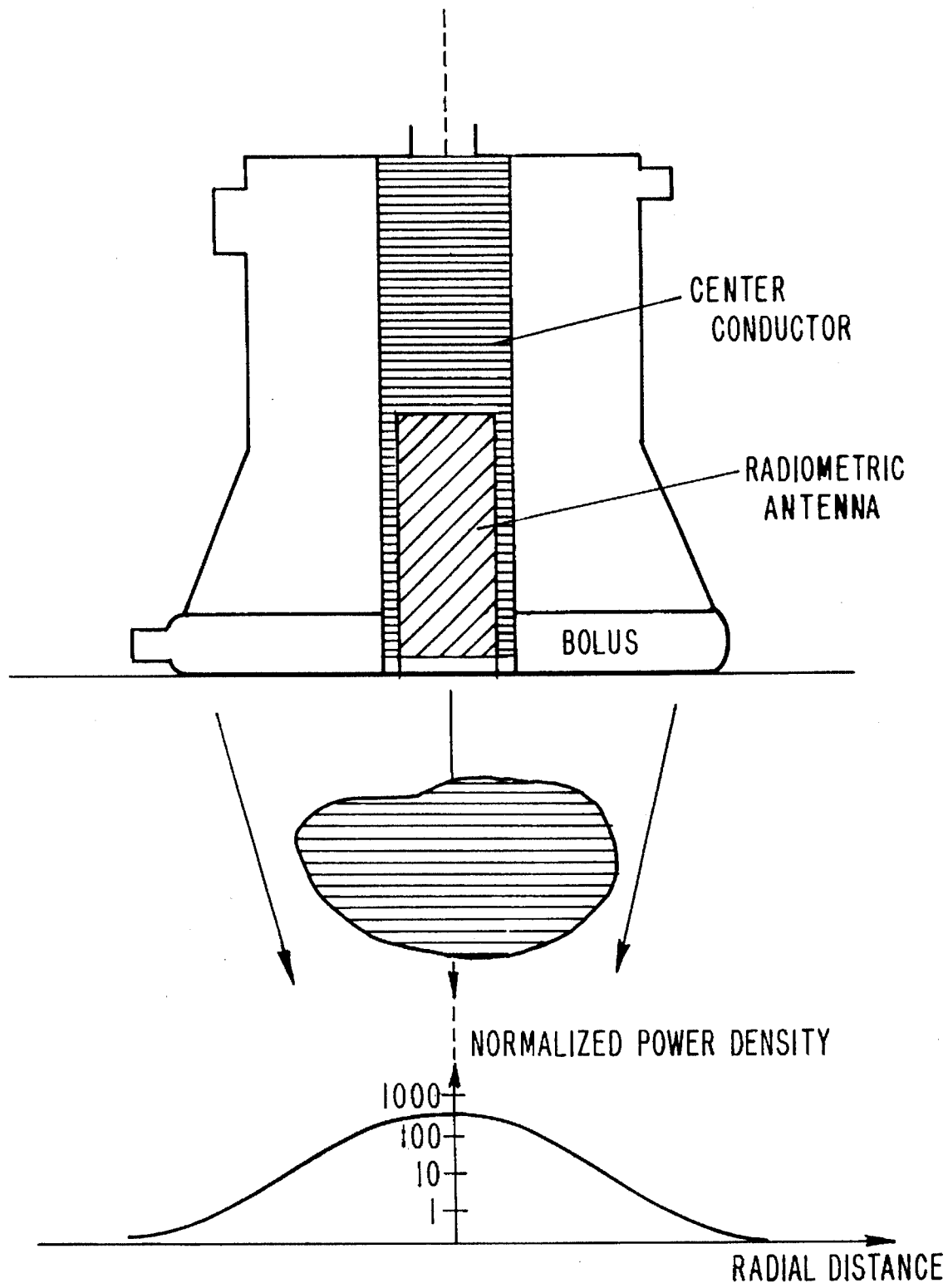
FIG. 4 depicts a plot of the radiation pattern relative to the applicator shown in FIG. 2.

FIG. 3 depicts a cross-sectional view of the modified horn. In cross-section, the outer conductor 18 is concentric to inner/center conductor 6. The non-conducting, e.g., non-metallic, supports 54 hold inner conductor 6 in place relative to the outer conductor 18. The preferred embodiment positions the non-metallic supports 54 at approximately ⅔ the length of the inner conductor 6, as measured from the shorting-end conductor 56. A total of three non-conducting supports 54 are depicted in FIG. 3, but the number can be varied. The underlying principal is that at least one non-conducting support 54 supports the inner conductor 6 relative to the outer conductor 18 in a bicycle wheel fashion. For example, non-metallic supports 54 can hold inner conductor 6 in place by being attached to a non-conducting ring surrounding the coaxial inner conductor 6 and each non-conducting support can be attached to the outer conductor 18 by a suitable attachment device such as screws. Inner conductor 6 attaches to the shorting-end conductor 56 by an electrical connection, such as metallic screws or welding. The modified horn's exterior shape is formed by outer conductor 18.

Figure 5:
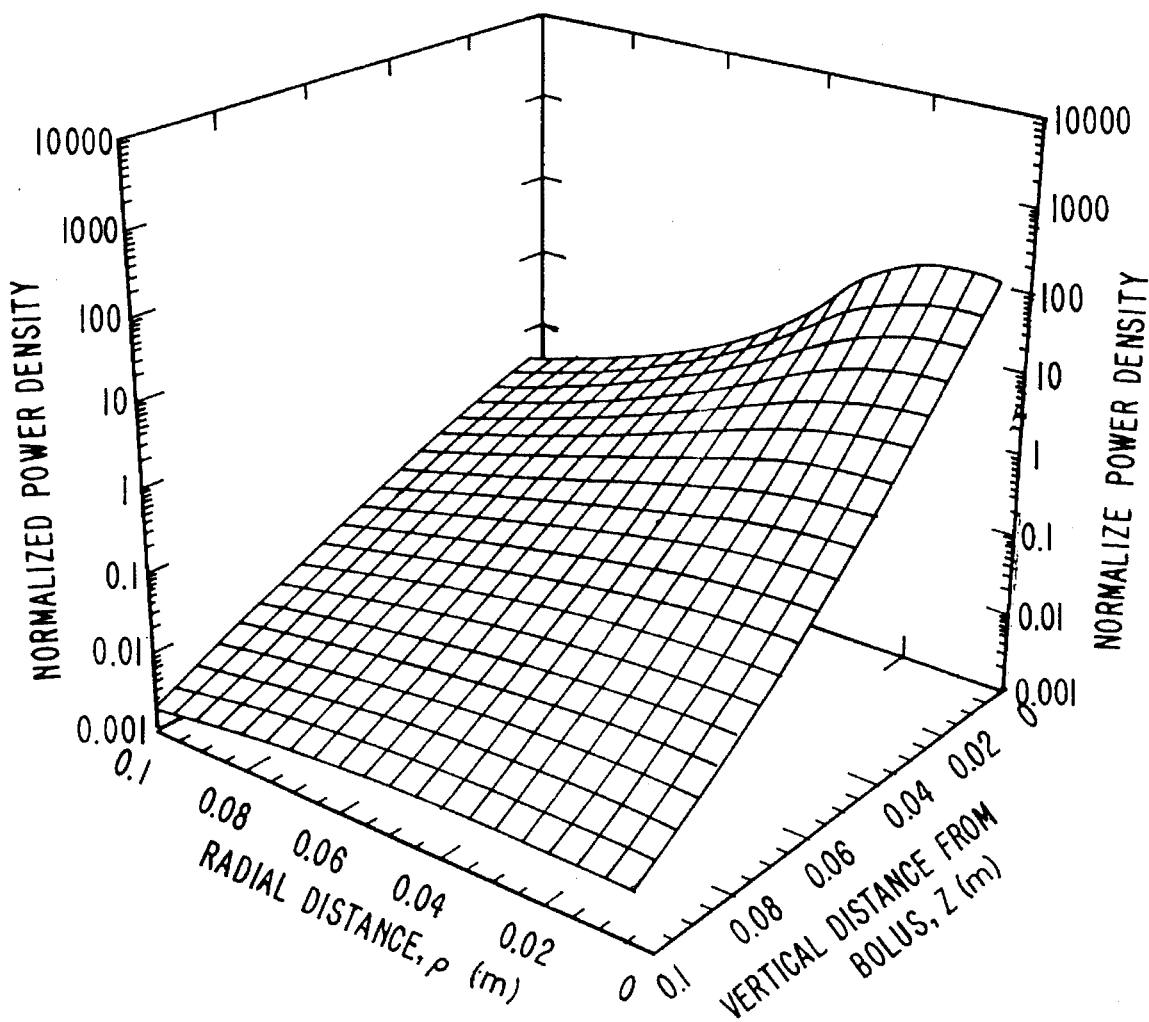
FIGS. 5–8 depict performance plots of particular examples of the preferred embodiment shown, for example in FIG. 2.
Figure 6:
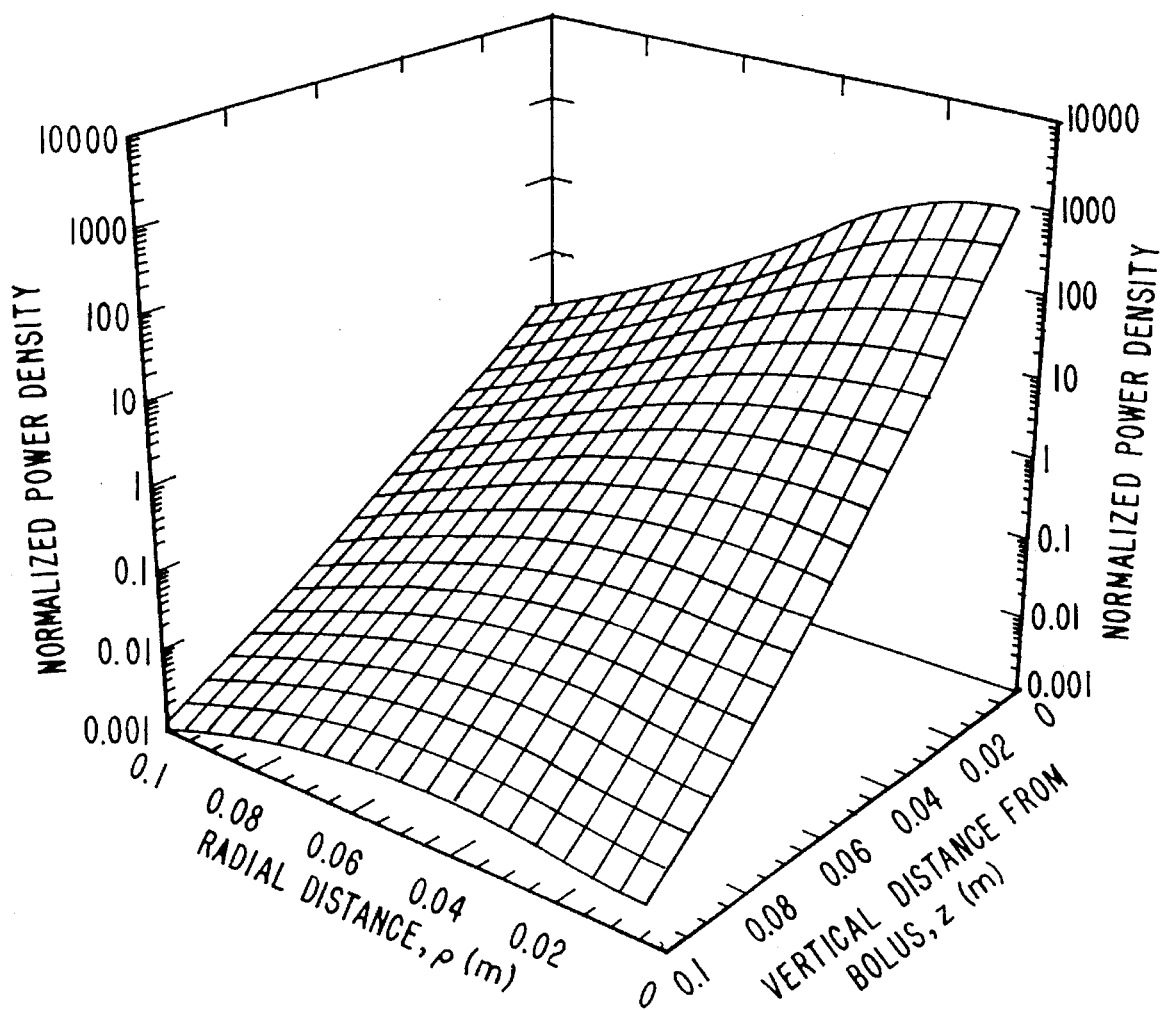
Figure 7:
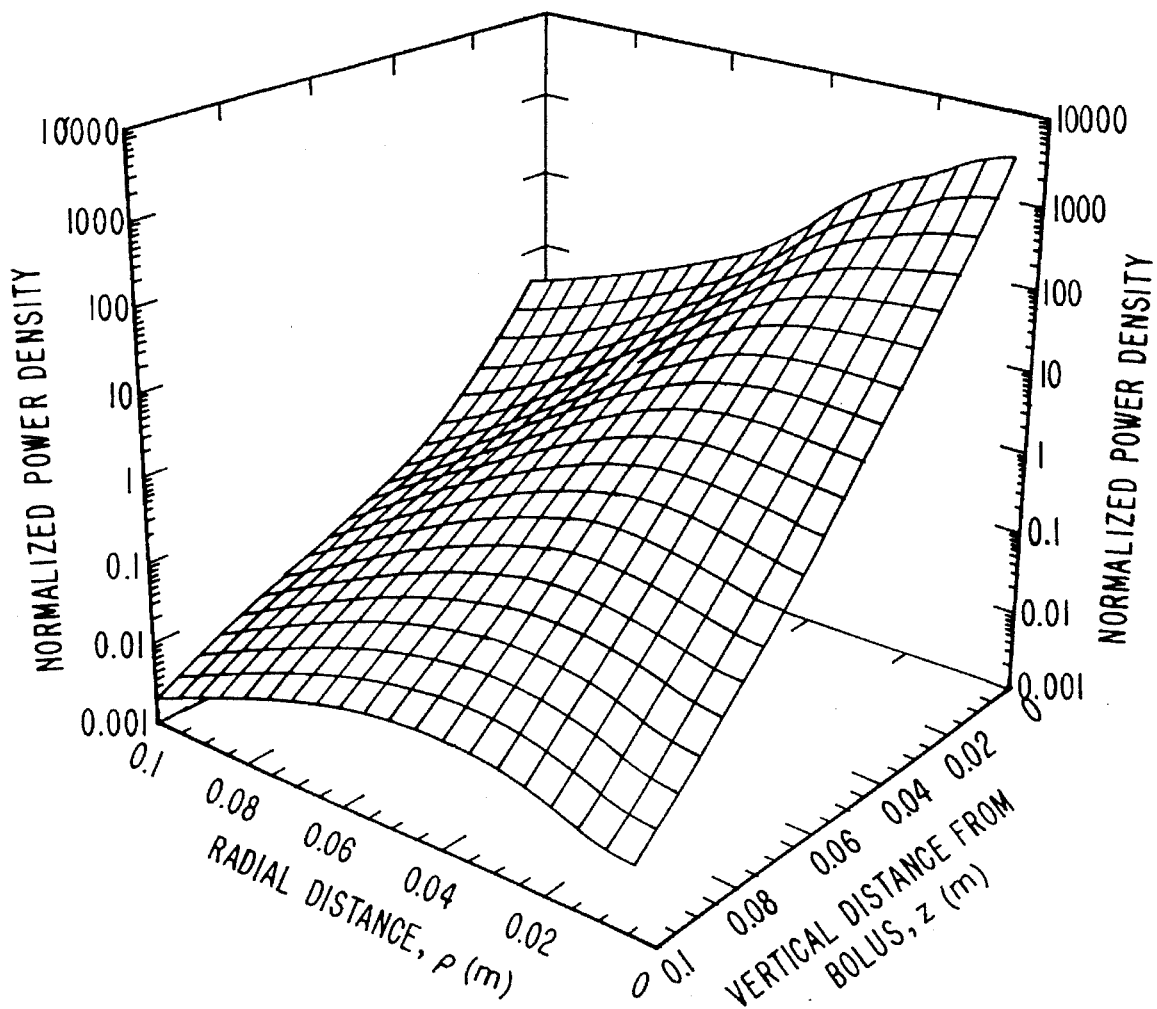
Figure 8:
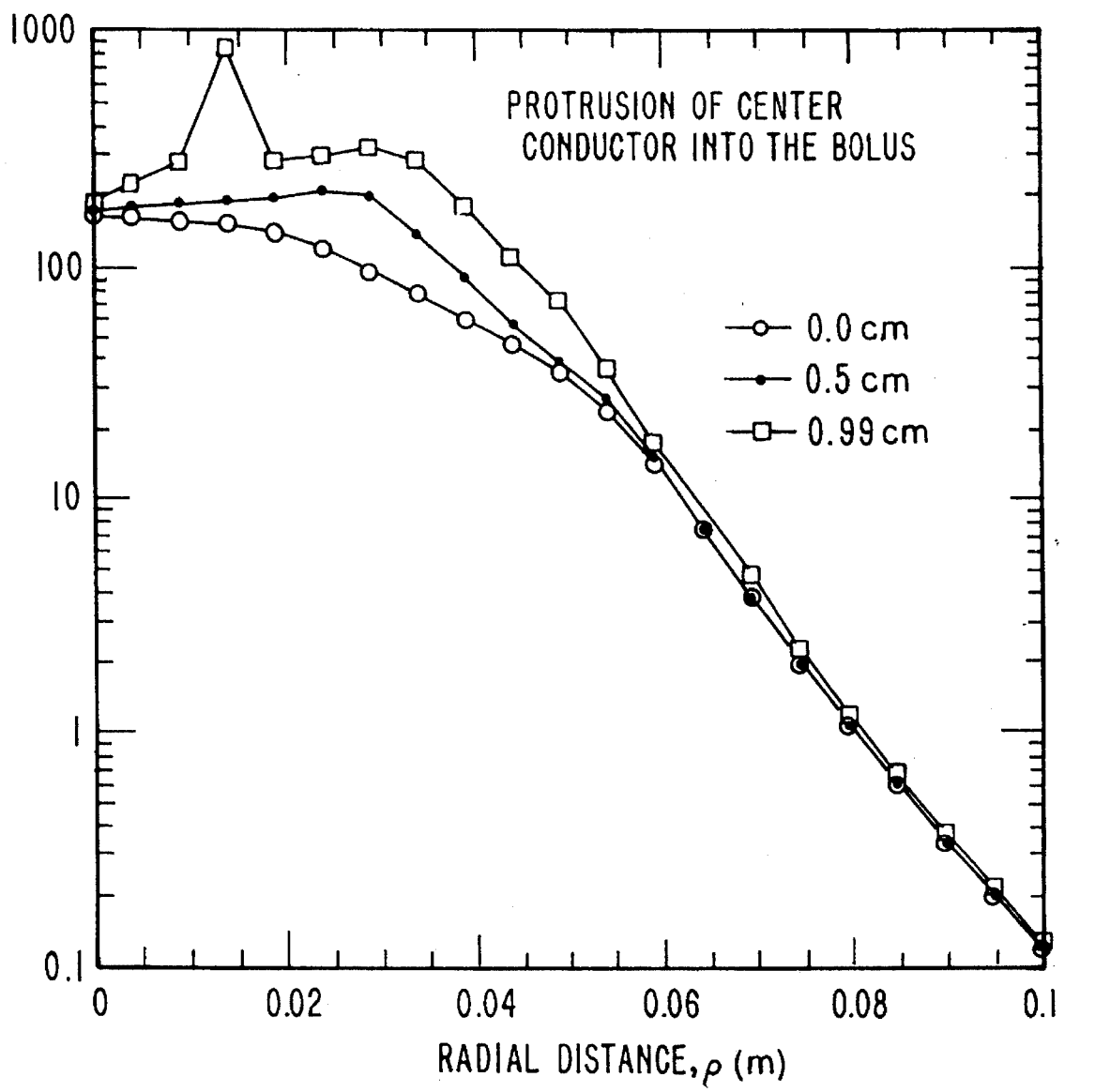

The presence of the coaxial inner conductor is what makes the horn into a modified horn. The modified horn achieves the beneficial result that the TEM mode of energy propagation deposits energy in a bell-shaped distribution or radiation pattern. Energy is concentrated in an area where the tumor is located, resulting in minimal heating of surrounding healthy tissue. FIG. 5 depicts a three-dimensional plot of normalized power distribution in the body 16 versus radial distance and versus vertical distance from the bolus 14 at a frequency of 100 MHz, for an outer conductor 18 radius of 3 cm, and inner conductor 6 radius of 1.5 cm, a protrusion distance of the inner conductor 6 into the bolus 14 of zero, and a 1 cm thick bolus 14 layer. FIGS. 6–7 depict similar plots except that the frequency for FIG. 6 is 500 MHz and the frequency for FIG. 7 is 900 MHz. FIG. 8 depicts the normalized power density as a function of radial distance along the body interface 22 for various protrusion distances of the inner-conductor 6 into the bolus 14, using the same applicator as that used in FIG. 5.

The radiometric antenna (receiving antenna) includes its own dielectric. This dielectric preferably is a solid low-loss dielectric and has a high dielectric constant (water has a dielectric constant of 78 and would be ideal, but a solid material with a dielectric constant of 30 is used instead because it has a very low loss factor). The applicator itself has a liquid dielectric which is deionized water. Deionized water has a high loss at microwave frequencies and cannot be used in the radiometric antenna which is used to make very sensitive measurements. The high loss causes the applicator portion to heat up, thereby necessitating the liquid dielectric circulation discussed above.

An aperture 20 of the coaxial-configured application antenna 8 is located flush against the surface of the bolus 14, the bolus 14 contacting the body interface 22. The signal source line 44 for the applicator 8 is shown entering the applicator 8 through source signal port 45.

An electromagnetic radiation propagation axis 24 is shown extending into the body 16 directly beneath the applicator 8, substantially perpendicular to the body interface 22. A tumor 30 is shown directly beneath the applicator 8 being irradiated by delivered EM energy 48. Thermal EM energy 50 is shown radiating from the tumor 30.

The radiometric, i.e., receiving, antenna 10 is located interior to the inner conductor 6, as depicted in both FIGS. 2–3. It is noted that the applicator 8 functions substantially the same regardless of the presence of the receiving antenna 10 interior to the inner conductor 6.

Figure 9:
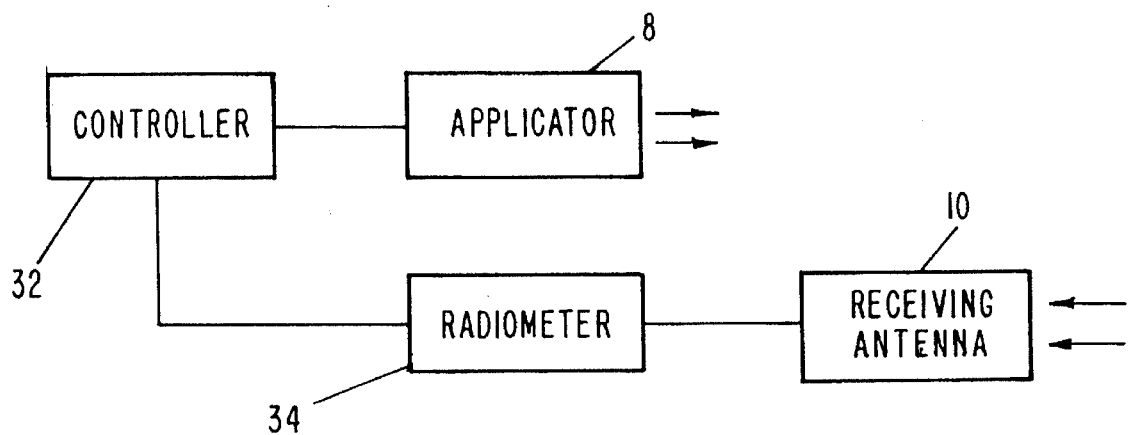
FIG. 9 depicts the feedback control of the preferred embodiments shown in FIG. 1.

The operation of the non-invasive hyperthermia applicator 8 and non-invasive radiometric antenna 10 will be explained next. As depicted in FIG. 9, the transmitting antenna 8 applies microwave frequency energy non-invasively to the tumor volume 30. The actual size of the applicator may be the same for all three frequencies, but the size will be chosen for the best conformity to the human body and the size tumor that is being treated. A frequency band that achieves good penetration includes the range 200 MHz≦f≦1000 MHz. To conform with the medical frequencies authorized in the U.S.A., Japan, and Europe, the frequency should be either substantially 200, 434, or 915 MHz, respectively.

Maintaining dielectric 12 at a constant temperature prevents overheating. The microwave energy that passes through the antenna will heat up the dielectric (water) that is circulating throughout the antenna. If not controlled, the temperature of the dielectric would continue to increase to undesired levels. In that circumstance, the interior of the transmitting applicator could heat up and could damage the structure of the applicator. Also, such a circumstance might be very uncomfortable to, or may burn, the patient's skin surface against which is placed the applicator. Also, in that circumstance, the temperature of the receiving (radiometric) antenna might increase, thus possibly adding unwanted variance into the noise figure.

Figure 10:
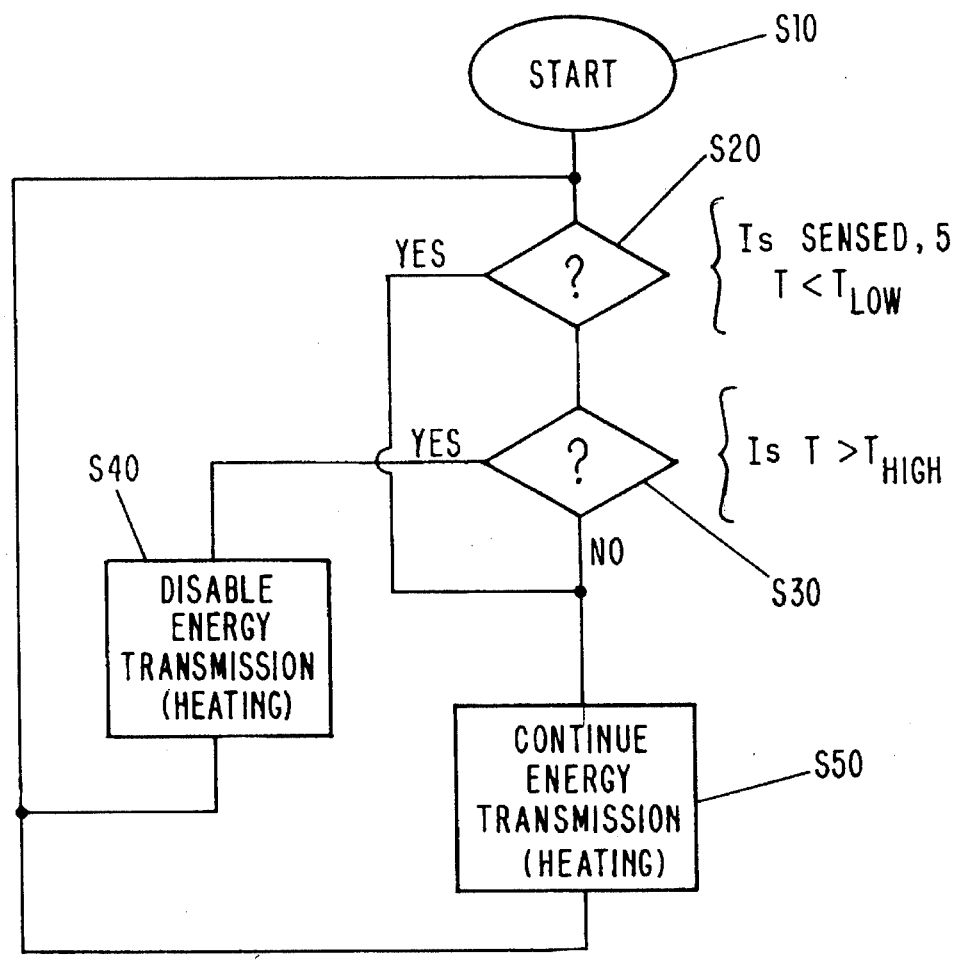
FIG. 10 depicts a feedback control flowchart for the control shown in FIG. 8.

FIG. 10 depicts the feedback control used in the preferred embodiment. Feedback control starts at step S10. Next at step S20, it is determined whether the sensed temperature, T, is less than a lower bound ($T<T_{low}$). If T is less than $T_{low}$, then flow skips to step S50 in which energy transmission, i.e., heating, is directed to continue. Flow exits step S50 and returns to step S20. If T is greater than or equal to $T_{low}$, flow proceeds to step S30 in which it is determined whether sensed temperature is greater than an upper bound ($T>T_{high}$). If T is greater than $T_{high}$, then flow proceeds to step S40 in which energy transmission (heating) is directed to be disabled. Flow proceeds from step S40 back to step S20. If T is less than or equal to $T_{high}$, then flow proceeds to step S50. Reference temperatures $T_{low}$ and $T_{high}$ will vary in the range 40°≦T≦44° C. depending upon the duration desired for the radiation to be applied and upon the location of the body that is to be irradiated.

The Controller 32, preferably a programmed digital computer, reads the voltage output by the radiometer 34 (which receives a radiometric signal from the radiometric antenna 10) and converts the voltage to temperature. Using the temperature, it implements at least the steps described in FIG. 10. Of course, the controller could be implemented alternatively using either discrete digital or analog electronics.

The receiving antenna 10 alternates operation with the transmitting antenna 8 and monitors non-invasively a temperature of the tumor using single or multifrequency microwave radiometry, preferably sensitive over the frequency range of 1–4 GHz. An inherent advantage of radiometry is that it eliminates the need for invasive, i.e., traumatic, thermometry.

With the radiometric antenna 10 integrated within the applicator 8, the resulting device is dual-functioning, i.e., it functions both as a hyperthermia heating energy emitter and as a non-invasive radiometric subcutaneous temperature sensor. The maximum energy deposition or radiation pattern produced by the coaxial-configured application antenna 8, discussed above, occurs directly beneath the receiving antenna 10. This maximum deposition area is co-located with the maximal sensitivity area of receiving antenna 10, thus providing temperature information for the region elevated to the highest temperature. This co-location achieves the advantage that the highest temperature region is monitored for feedback control of the heat delivery system.

Transmitting and receiving by the applicator having the radiometric antenna integrated therein preferably is not conducted simultaneously because the energy emitted by applicator 8 interferes, i.e., affects, the thermoelectromagnetic emissions collected by the receiving antenna 10. Consequently, the transmitting antenna 8 and receiving antenna 10 are operated in a time-share fashion, i.e., are controlled by the controller 32 so that transmission and reception are conducted mutually exclusively.

The aperture 20 of applicator 8 is preferably at a substantially constant distance of 1 cm away from the body interface 22 separated by the bolus 14. The only dimension that can be varied is the protrusion distance of the radiometric antenna 10 into the 1 cm bolus 14.

The best protrusion distance for the radiometric antenna 10 is 1 cm into the bolus 14, which places it firmly against the body interface, as shown in FIG. 2, for example. This position minimizes unwanted external noise interfering with, and maximizes the EM energy received by, the radiometric antenna 10.

Figure 11:
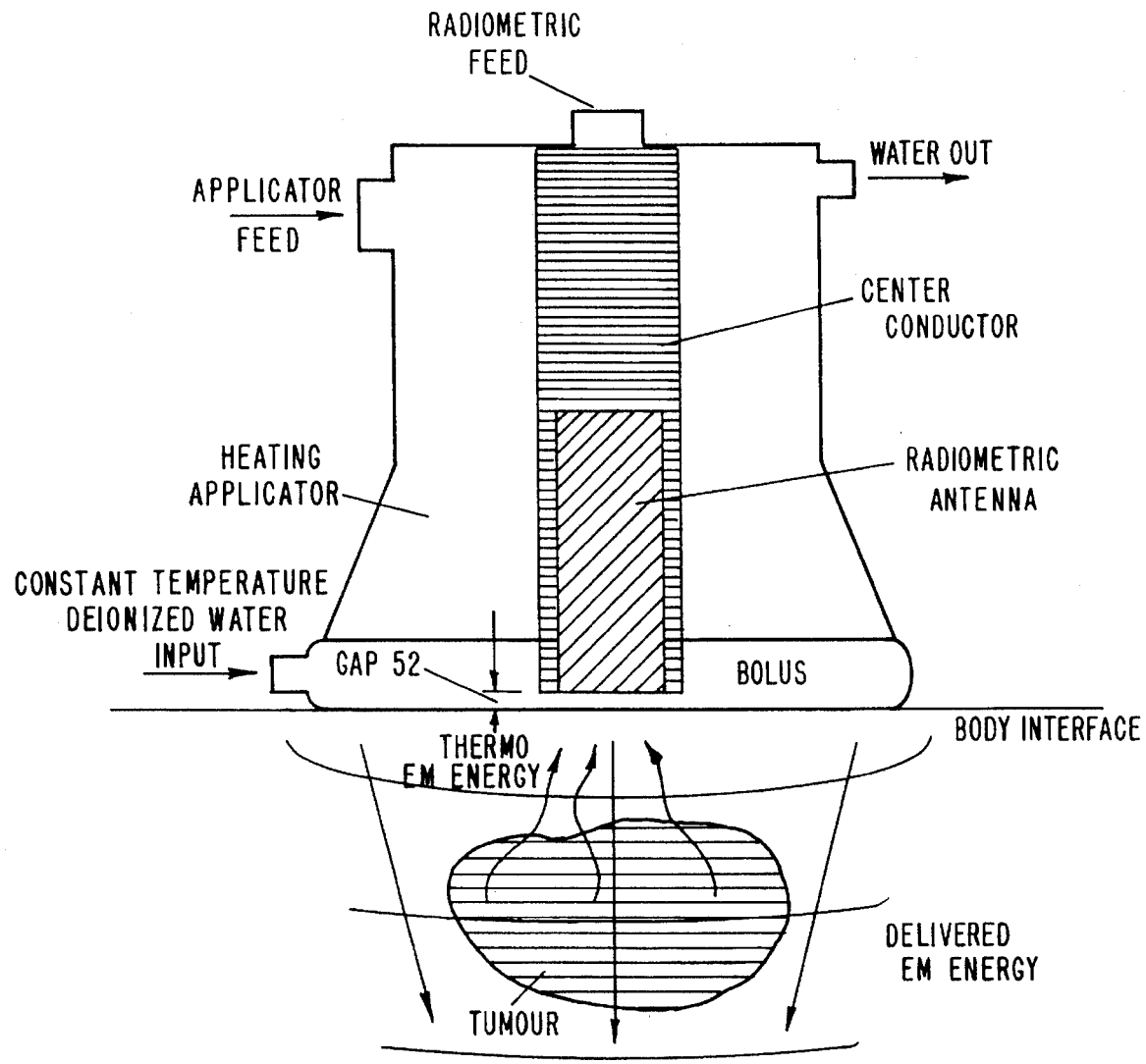
FIG. 11 depicts an alternative preferred embodiment to FIG. 2.

Another preferred embodiment is shown, for example, in FIG. 11. FIG. 11 is identical to FIG. 2 except for the presence of gap 52. The inner conductor 6 does not protrude beyond aperture 20 so far that it touches the body interface 22. Instead, a gap 52 is left therebetween. A different protrusion distance of less than 1 cm into the bolus 14 (leaving gap 52), reduces the efficiency of the radiometric portion of this dual-function antenna for example. However, by adjusting the protrusion distance between 0 and 1 cm, the heating pattern of the applicator will change slightly. For certain applications, it may be desirable to vary the protrusion distance to alter thereby the heating pattern. The change in efficiency occurs due to changes in the fields that extend across the aperture 20 of the applicator 8 from the outer conductor 18 to the inner conductor 6, caused by the change in the protrusion distance.

Without the inner conductor 6, the applicator 8 no longer produces a TEM mode of propagation having the single central maxima, described above. Instead, it is changed into a mere circular waveguide antenna having a broad radiation pattern. In contrast, the particular TEM mode radiation pattern produced by modified horn applicator 8 is less broad and concentrates its energy in the center rather than in plural maxima.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. A hyperthermia apparatus including a coaxial applicator for applying non-invasively inputted electromagnetic energy to a body surface against which the apparatus is placed, comprising:

said coaxial applicator having a central axis of symmetry that is adapted to be placed substantially perpendicular to the body surface including:

an inner conductor in the shape of a first surface of revolution about the axis of symmetry in the form of a first cylinder, the inner conductor forming an inner cavity interior thereto;

an outer conductor in the shape of a second surface of revolution about the axis of symmetry in the form of a modified cylinder, the outer conductor being coaxial outside the inner conductor;

a shorting-end conductor, the shorting-end conductor connecting a first end of the inner conductor to a first end of the outer conductor with the shorting end conductor disposed perpendicular to the axis of symmetry;

a diameter of the first end of the outer conductor being less than or equal to a diameter of a second end thereof opposite the first end such that the modified cylinder flares outwardly at the second end;

a bolus interface adapted to be disposed approximately parallel between the second end of the outer conductor and the body surface and connected to the second end of the outer conductor, the inner, outer and shorting-end conductors and the bolus interface forming an outer cavity, the outer cavity being filled with an applicator dielectric;

the coaxial applicator radiating inputted electromagnetic energy in a transverse electromagnetic (TEM) mode of propagation from the second end, a radiation pattern for the applicator being a bell-shaped curve symmetric about the axis of symmetry.

2. A hyperthermia apparatus as in claim 1, wherein:

the applicator-dielectric is liquid; and further comprising:

a pump for circulating the applicator-dielectric.

3. A hyperthermia apparatus as in claim 2, wherein:

the pump is external to the outer cavity and has a fluid connection to the bolus interface and to one of the inner, outer, and shorting-end conductors.

4. A hyperthermia apparatus as in claim 2, further comprising;

an applicator-dielectric temperature regulator.

5. A hyperthermia apparatus as in claim 4, wherein:

the temperature regulator regulates a temperature of the applicator-dielectric to be substantially constant as a function of controlling the pump.

6. A hyperthermia apparatus as in claim 1, further comprising;

an applicator-dielectric temperature regulator.

7. A hyperthermia apparatus as in claim 6, wherein:

the temperature regulator regulates a temperature of the applicator-dielectric to be substantially constant.

8. An apparatus as in claim 1, wherein:

the applicator dielectric has a permittivity substantially equal to a dielectric of the human body.

9. A hyperthermia apparatus including a coaxial applicator for applying non-invasively inputted electromagnetic energy to a body surface against which the apparatus is placed, comprising:

said coaxial applicator having a central axis of symmetry that is adapted to be placed substantially perpendicular to the body surface including:

an inner conductor in the shape of a first surface of revolution about the axis of symmetry in the form of a first cylinder, the inner conductor forming an inner cavity interior thereto;

an outer conductor in the shape of a second surface of about the axis of symmetry in the fore of a modified cylinder, the outer conductor being coaxial outside the inner conductor;

a shorting-end conductor, the shorting-end conductor connecting a first end of the inner conductor to a first end of the outer conductor with the shorting end conductor disposed perpendicular to the axis of symmetry;

a diameter of the first end of the outer conductor being less than or equal to a diameter of a second end thereof opposite the first end such that the modified cylinder flares outwardly at the second end;

a radiometric antenna receiving thermoelectric emissions, located within the inner cavity, and outputting a radiometric signal;

the coaxial applicator radiating inputted electromagnetic energy in a transverse electromagnetic (TEM) mode of propagation from the second end, a radiation pattern for the applicator being a bell-shaped curve symmetric about the axis of symmetry.

10. A hyperthermia apparatus as in claim 9 further comprising:

a controller, operatively connected to the applicator and responsive to the radiometric antenna, for controlling radiation of the inputted electromagnetic energy by the applicator as a function of the radiometric signal.

11. A hyperthermia apparatus as in claim 10, wherein:

the controller determines temperature within the body as a function of the radiometric signal.

12. An apparatus as in claim 9, wherein:

the apparatus receives thermoelectromagnetic emissions over a frequency range of substantially 1–4 GHz.

13. A hyperthermia apparatus as in claim 9 wherein:

the radiometric antenna is a waveguide having a rectangular cross-section substantially parallel to the shorting-end conductor.

14. A hyperthermia apparatus as in claim 9 wherein:

the radiometric antenna includes within it receiver dielectric.

15. A hyperthermia apparatus as in claim 14 wherein:

the receiver dielectric is a solid, low-loss dielectric having a dielectric constant of approximately 30.

* * * * *